United States Patent [19]

Kuehne

[11] 4,267,330

[45] May 12, 1981

[54] PROCESS FOR THE SYNTHESIS OF VINCADIFFORMINE AND RELATED DERIVATIVES

[75] Inventor: Martin E. Kuehne, Burlington, Vt.

[73] Assignee: Omnium Chimique Societe Anonyme, Brussels, Belgium

[21] Appl. No.: 936,454

[22] Filed: Aug. 24, 1978

[51] Int. Cl.³ .................. C07D 471/14; C07D 487/04
[52] U.S. Cl. .................... 546/51; 260/245.7; 260/326.5 B; 260/326.9; 260/343.5; 260/348.57; 260/348.58; 260/326.37; 546/223; 560/226; 568/484; 568/495
[58] Field of Search ............... 546/51; 260/326.37, 260/245.7

[56] References Cited

U.S. PATENT DOCUMENTS

| | | | |
|---|---|---|---|
| 3,525,750 | 8/1970 | Renner | 260/245.7 |
| 4,146,643 | 3/1979 | Pfäffli | 424/262 |
| 4,154,943 | 5/1979 | Kuehne | 546/51 |
| 4,220,774 | 9/1980 | Kuehne | 546/51 |

OTHER PUBLICATIONS

Kuehne et al., (I), J. Org. Chem., vol. 43, No. 19, pp. 3702–3704 (9/15/78).
Kuehne et al., (II), J. Org. Chem., vol. 43, No. 19, pp. 3705–3710 (9/15/78).
Kuehne et al., (III), J. Org. Chem., vol. 44, No. 7, pp. 1063–1068 (3/30/79).
Wang, Dissertation Abstracts, vol. 26, (3), p. 1361 (1965).
Kutney et al., J.A.C.S. 90, 3891 (1968).

*Primary Examiner*—Donald G. Daus
*Assistant Examiner*—Diana G. Rivers
*Attorney, Agent, or Firm*—Pollock, Vande Sande & Priddy

[57] ABSTRACT

This invention relates to the preparation of vincadifformine and related derivatives which are useful as starting material for the synthesis of vincamine and other related compounds possessing interesting psychopharmacologic properties.

A N-benzyl-tetrahydro-γ-carboline compound (III) is halogenated with t-butyl hypochlorite to obtain a haloindolenine compound which is directly treated with a metal dialkyl malonate such as thallium dialkyl malonate to provide a dialkyl 3-benzyl-1,2,3,4,5,6-hexahydroazepino (4,5-b) indole-5,5-dicarboxylate compound, said latter compound being hydrogenated to provide a dialkyl 1,2,3,4,5,6 hexahydroazepino (4,5-b) indole-5,5-dicarboxylate, said latter compound being condensed with a functionalized aldehyde, typically a haloaldehyde, to provide vincadifformine or a related derivative by passing through an intermediate compound being a salt of a dialkyl 3,3-(alkenyl)-1,2,3,4,5,6-hexahydroazepino(4,5-b) indolinium-(5,5)-dicarboxylate.

29 Claims, No Drawings

PROCESS FOR THE SYNTHESIS OF VINCADIFFORMINE AND RELATED DERIVATIVES

The present invention relates to a synthesis process for vincadifformine and related derivatives, and to intermediates produced in the process.

The compounds prepared by the process of the invention are of the general formula I.

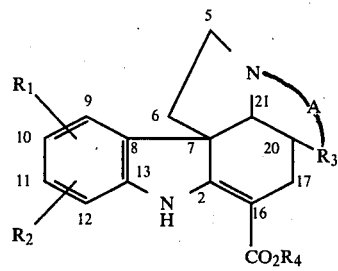

Ia  $R_1 = R_2 = H$  $R_3 = CH_2—CH_3$  $A = —(CH_2)_3—$
    $R_4 = CH_3$
Ib  $R_1 = 11\text{-}OCH_3, R_2 = H, R_3 = CH_2—CH_3, R_4 = CH_3$
    $A = —(CH_2)_3—$
Ic  $R_1 = R_2 = H$  $R_3 = CH_2—CH_3, R_4 = CH_3$
    $A = —CH_2—CH(OH)—CH_2—$
Id  $R_1 = R_2 = H, R_3 = CH_2—CH_3, R_4 = CH_3$ $$\diagdown N—A— = —N—CH(CH_2OH)—CH_2—$$

Ie  $R_1 = R_2 = H$  $R_3 = H, R_4 = CH_3$
    $A = —CH_2—CH(CH_2—CH_3)—CH_2—$

In the above general formula, $R_1$ and $R_2$ are the same or different, being selected from the group consisting of hydrogen, hydroxy, acyloxy, carbamate, halo, lower alkoxy or alkyl radical, $R_3$ and $R_4$ are lower alkyl or hydrogen, or a combination of such radicals. A represents an alkyl chain containing from 1 to 5 carbon atoms, and which may be substituted by a lower alkyl or hydroxy-alkyl group.

The term "lower alkyl" as used herein contemplates saturated hydrocarbon radicals, branched or not, containing from one to seven carbon atoms.

The numbering of vincadifformine and its derivatives is in accordance with Le Men and Taylor, Experienta 1965, 21, 500.

Examples of compounds which are prepared in accordance with the present invention are those of formulae Ia, Ib, Ic, Id and Ie as defined hereabove.

Vincadifformine of the formula Ia is an alkaloid which is the raw material for the preparation of the vincamine group alcaloids as described in Belgian Pat. Nos. 772,005 and 848,475.

Vincamine and some of its derivatives are well-known alkaloids used in human therapeutics as psychotropic drugs of high efficiency and possessing a relatively low order of toxicity.

Furthermore, it has been shown that the rearrangement of vincadifformine leading to vincamine may be applied to a large number of other similar derivatives to provide vincamine related compounds (see French Pat. applications No. 76 22335, No. 76 22275 and Belgian Pat. No. 816,692).

Two total synthetic methods for vincadifformine are already described in the literature by J. Kutney et al J.Amer.Chem.Soc. 90, 3891, 1968 and J. V. Laronze et al, Tetrahedron Letters 491, 1974.

A further method of total synthesis of vincadifformine is described and claimed in applicant's U.S. patent application Ser. No. 865,657 filed on Dec. 29, 1977, now U.S. Pat. No. 4,154,943.

11-methoxy vincadifformine (ervinceine) of the formula Ib is an alkaloid occuring in Vinca Erecta and described by D. A. Rakhimov, V. M. Malikov, M. R. Yagudaev and S. N. Yunusov (Khim, prir.Soedin. 226, 1970).

Pseudo-vincadifformine of formula Ie is an alkaloid occuring in different Apocynacea and which has been obtained by hemisynthesis (J. P. Kutney, E. Piers and R. T. Brown, J.Amer.Chem.Soc. 92, 1700, 1970).

The present invention aims to obtain vincamine and related polycyclic compounds with high yields, reducing the number of intermediate steps and using cheap reagents.

Therefore, the starting raw material used is a N-benzyltetrahydro-γ-carboline or 2-benzyl-1,2,3,4-tetrahydro-γ-carboline of the general formula III:

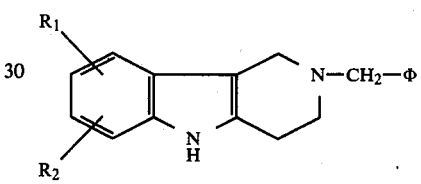

IIIa $R_1=R_2=H$
IIIb $R_1=11\text{-}OCH_3, R_2=H$ wherein $R_1$ and $R_2$ have the same meaning as described above and Φ represents a phenyl radical.

These compounds can be advantageously obtained from N-benzylpiperidone, a cheap compound of the formula

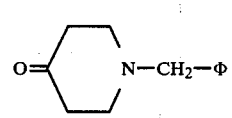

by passing through a N-benzylpiperidone phenylhydrazone of the general formula II

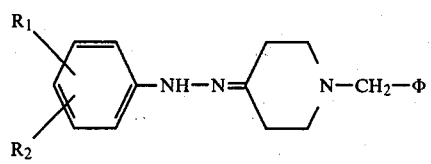

and reacting said latter compound under the conditions of the "Fisher Indole Synthesis".

According to the invention, N-benzyl-tetrahydrocarboline derivative (III) is transformed, in a first step, through the action of t-butyl hypochlorite or a similar chlorinating agent into the corresponding chloroindolenine of the general formula:

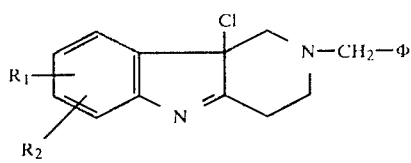

which is directly treated with a dialkyl thallium, sodium or analogous malonate, typically the diethyl or dimethylderivative, to yield a 3-benzyl-1,2,3,4,5,6-hexahydroazepino(4,5-b)indole-5,5-di(alkyl carboxylate) derivative of the formula V

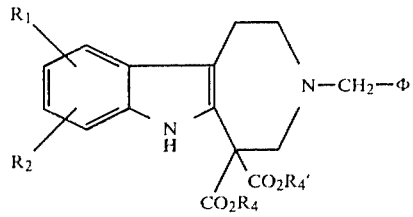

Va $R_1=R_2=H$
$R_4=R_4'=CH_3$
Vb $R_1=11\text{-}OCH_3$, $R_2=H$
$R_4=R_4'=CH_3$ wherein $R_1$, $R_2$ and $R_4$ are as defined above. $R_4'$ is a lower alkyl group, typically a methyl, ethyl or t-butyl radical.

For this condensation, any solvent inert to the reaction conditions may be used. Benzene and toluene are especially convenient and practical for this use.

In a second step, derivative V is hydrogenated in the presence of a catalyst, typically 5% Pd on charcoal, to remove the protecting benzyl group, yielding a dialkyl 1,2,3,4,5,6-hexahydroazepino(4,5-b)indole-5,5-dicarboxylate derivative of the general formula VI

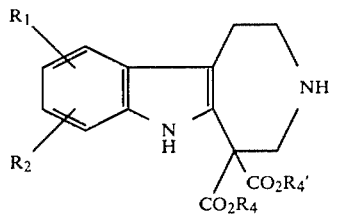

VIa $R_1=R_2=H$
$R_4=R_4'=CH_3$
VIb $R_1=11\text{-}OCH_3$, $R_2=H$
$R_4=R_4'=CH_3$ In a third step, derivative VI is condensed with a functionalised aldehyde VII yielding vincadifformine or related derivatives of formula (I).

By functionalised aldehyde it is understood an aldehyde for which a corresponding tertiary enamine derivative may be N-alkylated intra-molecularly.

Typically such compounds are halo, aryl or alkylsulfoxy, or epoxy aldehydes having three to fourteen carbon atoms.

Examples of such aldehydes are 5-bromo-2-ethyl-pentanal VIIa, 5-chloro-2-ethyl-pentanal, 5-sulfomethoxy-2-ethyl pentanal, 4-(bromomethyl)hexanal VIIb, 2-ethyl-4-oxyranyl pentanal VIIc.

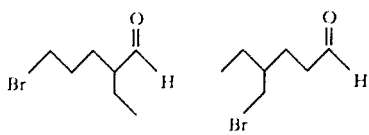
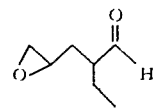

In the case of the reaction of a haloaldehyde with the azepino indole VI, the intermediate compound of general formula VIII may be isolated. In formula VIII, $X^-$ represents a halide ion, typically bromide ion. This ion can be exchanged to give the derivative where $X^-$ is a tetraphenylborate ion.

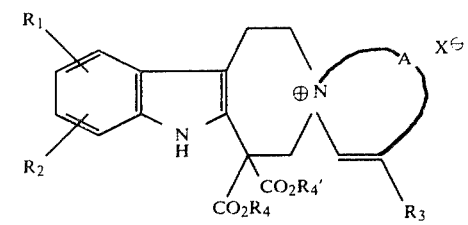

In effecting the condensation (VI+aldehyde through VIII) it has been found preferable to use a solvent such as dry methanol, but other inert solvents to the reaction conditions may be used.

The temperature of the reaction may vary from $-20°$ C. to the boiling point of the reaction medium. Preferred temperature ranges include 20° to 40° C.

Alternatively, intermediates V or VI may be monodecarboalkoxylated to yield the monoester amine (IXa or IXb), which can be converted to vincadifformine or derivatives thereof in accordance with the applicant's U.S. patent application Ser. No. 865,657, filed Dec. 29th, 1977.

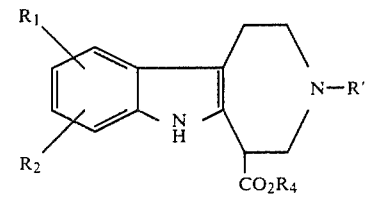

IXa $R_1 = R_2 = H$ $R_4 = CH_3$
IXb $R_1 = 11\text{-}OCH_3$, $R_2 = H$
$R_4 = CH_3$ 5-bromo-2-ethylpentanal which can be used in the last step of the vincadifformine synthesis may be prepared following a hitherto undisclosed process which is both practical and convenient.

One acetalises methyl or ethyl 4-formylhexanoate to yield respectively methyl or ethyl 4-dimethoxymethyl-hexanoate which is reduced by means of lithium aluminium hydride into respectively 4-dimethoxymethyl-1-hexanol or 4-diethoxy-methyl-1-hexanol.

The alcohol obtained in this way is dehydroxybrominated yielding respectively 1-bromo-4-dimethoxymethyl-hexane and 1-bromo-4-diethoxymethyl-hexane, which is hydrolysed to yield the required 1-bromo-4-formylhexane or 5-bromo-2-ethylpentanal.

Another preparation of 5-bromo-2-ethylpentanal is also disclosed in W. Oppolzer, H. Hauth, P. Pfaffli, R. Wenger, Helv. 60, 1861 (1977).

The following examples describe the characteristics of the invention in a non limitative way.

EXAMPLE 1

N-benzyl-4-piperidone phenylhydrazone (IIa)

To a solution of 600 ml of 1:1 $H_2O/EtOH$ was added N-benzyl-4-piperidone (38 g, 0.2 mol) and phenylhydrazine hydrochloride (32 g, 0.22 mol). The solution was stirred at room temperature for 48 hours and then made basic by the addition of saturated potassium carbonate (addition should be done at a rate which allows for control of the foaming). The product separated as an oil and was collected. The water layer was extracted with ethyl acetate, the combined organic fractions were dried ($MgSO_4$) and the solvent was removed under vacuum. Hexane (100 ml) was added and then removed under vacuum to help remove the remaining polar solvents. To the crystallizing product 200 ml of hexane was added and, after 20 min. vacuum filtration gave 50 g (87%) of the phenyl hydrazone (IIb) which was suitable for use in the next step. The product can be recrystallized from hexane; m.p. 80–81 [lit. 78°–79° C., see N. P. Buu-Hoi, O. Roussel and P. Jacquignon, J.Chem.-Soc. 708(1964)].

EXAMPLE 2

2-benzyl-1,2,3,4-tetrahydro-γ-carboline (IIIa)

N-benzylpiperidone phenylhydrazone (IIa, 49 g, 0.18 mol) was added with stirring to 250 ml of glacial acetic acid containing 7% by weight of anhydrous HCl. The solution immediately turned dark red and became quite hot. Stirring was continued until the solution had cooled to room temperature (15–20 min). The solution was then made basic by careful addition of saturated aqueous potassium carbonate and extracted with dichloromethane. After drying ($MgSO_4$) and solvent removal the residue crystallized. The product was washed with ethanol and then recrystallized from ethanol to give 29.5 g (65%) of N-benzyl-tetrahydro-γ-carboline; m.p. 158–159 [lit. 161° C., see N. P. Buu-Hoi, O. Roussell and P. Jacquignon, J.Chem.Soc. 708 (1964)].

NMR ($CDCl_3$): δ 2.6–3.0 (4H, m), 3.75 (2H, s), 3.81 (2H, s), 7.0–7.5 (9H, m), 7.8–8.0 (1H, broad singlet).

EXAMPLE 3

2-benzyl-7-methoxy-1,2,3,4-tetrahydro-γ-carboline (IIIb)

A solution of 5.0 g (0.0286 mol) of m-methoxyphenylhydrazine hydrochloride and 5.04 g (0.0267 mol) of N-benzyl-4-piperidone in 175 ml of 50% aqueous methanol was stirred under $N_2$ for 72 hours at 20° C. The solution was made basic by the addition of saturated aqueous $K_2CO_3$ whereupon the hydrazone separated as a brown oil. The mixture was transferred with ethyl acetate to a 1 l separatory funnel and the aqueous layer was separated and extracted twice with ethyl acetate. The combined organic layers were extracted twice with saturated brine, dried ($MgSO_4$), filtered, and the solvent was removed to yield a viscous brown oil. The crude hydrazone was dissolved in 50 ml of acetic acid and 140 ml of acetic acid saturated with HCl was added with vigorous stirring. The solution was stirred under $N_2$ in an oil bath at 90° C. for 30 min., cooled to 20° C. and made basic by addition of saturated aqueous $K_2CO_3$ with vigorous stirring (addition of 100 ml of ethyl acetate helps to control foaming). The mixture was transferred to a 1 l separatory funnel with 200 ml of ethyl acetate and 100 ml of water and the aqueous layer was separated and extracted twice with ethyl acetate. The combined organic layers were washed twice with saturated brine, dried ($MgSO_4$), and filtered. Removal of solvent left a brown gummy oil which crystallized on trituration with 95% ethanol. Recrystallisation from the same solvent and from methanol yielded 2.75 g (35%) of off-white crystals of compound (IIIb), m.p. 172°–173° C.

NMR [$CDCl_3$+DMSO ($D_6$)]δ: 10.30 (bs, 1H), 7.30 (m, 5H), 7.07 (d, 1H, J=8 Hz), 6.75, (d, 1H, J=2 Hz), 6.53 (d of d, 1H, J=8 Hz, 2 Hz), 3.71 (s, 3H), 3.70 (s, 2H), 3.53 (s, 2H), 2.75 (s, 4H).

IR (KBr): 3410, 1640, 1610, 1580 $cm^{-1}$.

Mass spectrum (80 eV) m/e 292 ($M^+$), 173 (Base).

Analysis calculated for $C_{19}H_{20}N_2O$: C, 78.09%; H, 6.90%; N, 9.58%; Found: C, 78.05%; H, 7.04%; N, 9.58%.

EXAMPLE 4

Dimethyl 3-benzyl-1,2,3,4,5,6-hexahydroazepino(4,5-b)indole-5,5-dicarboxylate (Va)

To a solution of 0.25 g (0.95 mmol) of N-benzyl-tetrahydro-γ-carboline (IIIa) and 110 μl of triethylamine in 7 ml dry benzene, stirring at 5° C. under nitrogen, was added dropwise 110 μl of tert-butylhypochlorite (0.954 mmol). The mixture was stirred at 5° C. for 1 hour 30 minutes, then poured into 3 ml of cold water in a separatory funnel. After gentle shaking the layers were allowed to separate and the $H_2O$ layer was discarded. The benzene layer was dried by filtering through a cone of sodium sulfate in phase separation paper. The separatory funnel and filter cone were washed with dry benzene and the benzene filtrate was evaporated under vacuum to 3 ml. Dry benzene was added to a volume of 7 ml, then 0.335 g (1 mmol) thallium dimethyl malonate was added and the vigorously stirring solution was refluxed under nitrogen for 23 hours. The reaction was then cooled to room temperature and filtered through glass fibre paper and the benzene was evaporated under vacuum. The residue was taken up in dichloromethane and deposited on a column of $SiO_2$ (1.5 cm × 30 cm). Elution with dichloromethane yielded 0.195 g (52%) of a slightly colored product which had IR and NMR spectra identical with those of the product obtained in 46% yield from N-benzyl-tetrahydro-γ-carboline by the same reaction sequence. Recrystallization from methanol afforded white crystals of product (Va), m.p. and mmp 166°–168° C.

NMR ($CDCl_3$, δ): 2.97 (s, 4H), 3.8 (s, 2H), 3.88 (s, 6H), 3.93 (s, 2H), 7.24–7.8 (m, 9H), 8.64 (bs, 1H).

IR (KBr, $\nu_{max}$): 3510, 3010, 3000, 2950, 2940, 2920, 2880, 2825, 1750, 1705, 1490, 1450, 1440, 1435, 1345, 1320, 1285, 1275, 1255, 1240, 1220 (broad), 1185, 1165, 1145, 1135, 1125, 1110, 1090, 1075, 1055, 1035, 980, 960, 935, 700, 690, 670, 635 $cm^{-1}$.

IR ($CHCl_3$, $\nu_{max}$): 3440, 3000, 1725, 1455, 1425, 1210 (broad) 1045, 1025, 975 $cm^{-1}$.

Mass spectrum (m/e) 392 (M+).

Analysis calculated for $C_{23}H_{24}N_2O_4$ Calculated: C 70.39%; H 6.16%; N 7.14%; Found: C 70.12%; H 6.25%; N 6.91%.

EXAMPLE 5

Dimethyl 3-benzyl-8-methoxy-1,2,3,4,5,6-hexahydroazepino(4,5-b)indole-5,5-dicarboxylate (Vb)

To a solution of 2.5 g (8.56 mmol) of the methoxytetrahydro-γ-carboline (IIIb) and 1.07 ml of triethylamine in 60 ml of dichloromethane, stirring under $N_2$ at −78° C., was added under the liquid surface, via syringe, 5 ml of a solution of 1.2 ml of t-butylhypochlorite in 4.4 ml of dichloromethane. The mixture was stirred for 15 min., then allowed to warm to 20° C. The solvent was removed under vacuum, leaving a viscous brown oil. Thin layer chromatography ($Al_2O_3$, $CH_2Cl_2$) showed clean conversion to the chloroindolenine.

The crude product was taken up in 50 ml of dry benzene, 3.45 g (0.0103 mol, 1.2 x) of thallium dimethyl malonate was added and the slurry was stirred vigorously under nitrogen for 2 hours at 20° C. and an additional 3.50 hours at reflux. The mixture was allowed to cool to 20° C. and saturated NaCl solution was added to precipitate TlCl. The mixture was filtered through glass fibre paper (GF/A) and the flask and filter cake were rinsed with benzene. The organic layer was separated and the aqueous layer was extracted with benzene. The combined benzene layers were washed with saturated brine, dried ($MgSO_4$) and filtered and the solvent was removed under vacuum to give a brownish solid. Crystallization from methanol yielded 2.19 g of white crystals. Chromatography ($SiO_2$, 5% MeOH in $CH_2Cl_2$) of the mother liquor yielded fractions containing the desired product which upon combination, solvent removal, and crystallization from MeOH with seeding yielded an additional 0.36 g of off-white crystals of product (Vb).

Total yield: 2.56 g (71%).

NMR ($CDCl_3$, δ): 8.29 (bs, 1H), 7.28 (m, 6H), 6.70 (d of d, 2H), 3.78 (s, 2H), 3.76 (s, 3H), 3.72 (s, 6H), 3.66 (s, 2H), 2.84 (s, 4H).

IR (KBr): 3462, 1790, 1635, 1575, 1515, 1905, 1255, 1220, 1210 cm⁻¹.

Mass Spectrum (80 eV) m/e: 422 (M+). An analytical sample recrystallized from MeOH had m.p. 132°–134° C.

Analysis calculated for $C_{24}H_{26}N_2O_5$ Calculated: C 68.23%; H 6.20%; N 6.63%; Found: C 67.9%; H 6.40%; N 6.45%.

EXAMPLE 6

Dimethyl 1,2,3,4,5,6-hexahydroazepino(4,5-b) indole-5,5-dicarboxylate (VIa)

To 1.6 g (4.08 mmol) of the diester benzylamine (Va) dissolved in 50 ml of acetic acid was added 0.2 g of 5% palladium on charcoal catalyst. Hydrogenation at atmospheric pressure with vigorous stirring showed termination of hydrogen uptake after 3 hours. The solution was filtered through glass fibre paper and the flask and filter were washed with dichloromethane. The dichloromethane was removed under water aspirator vacuum and the acetic acid was distilled on a vacuum pump with a dry ice/acetone trap. The residue was taken up in dichloromethane, washed with 10% aqueous sodium carbonate dried over potassium carbonate, filtered, and concentrated under vacuum to a white powder of product (VIa); 1.231 g (100%).

NMR ($CDCl_3$, δ): 2.4 (bs, 1H), 2.9 (t, 2H), 3.1 (t. 2H), 3.66 (s, 2H), 3.72 (s, 6H), 6.9–7.5 (m, 4H); 8.66 (bs, 1H)

Mass spectrum (m/e) 302 M+.

EXAMPLE 7

Dimethyl 8-methoxy-1,2,3,4,5,6-hexahydroazepino (4,5-b) indole-5,5-dicarboxylate (VIb)

A solution of 2.16 g (5.12 mmole) of N-benzyl amine (Vb) in 15 ml of acetic acid was stirred vigorously under $H_2$ at 1 atm., with 0.21 g of 10% Pd/C catalyst for 3 hours. The catalyst was filtered and washed with acetic acid. The solvent was removed under vacuum leaving a pale yellow oil which was taken up in 50 ml of dichloromethane. An equal volume of saturated aqueous $K_2CO_3$ was added and the mixture was stirred vigorously for 10 min. The organic layer was separated and the aqueous layer was extracted with 25 ml of dichloromethane. The combined organic extracts were dried over potassium carbonate, filtered, and the solent removed to yield 1.72 g (100%) of a white foam, which crystallized from methanol thus yielding the desired product VIb.

NMR ($CDCl_3$, δ): 8.76 (bs, 1H), 7.4 (d, 1H), 6.8 (m, 2H), 3.8 (s, 3H), 3.78 (s, 6H), 3.7 (s, 2H), 3.14 (m, 2H), 2.90 (m, 2H), 2.34 (s, 1H).

IR (KBr): 3405, 3395, 1755, 1730, 1640, 1600, 1275, 1255, 1235, 1210 cm⁻¹.

An analytical sample recrystallized from MeOH had m.p. 156°–157° C.

Analysis calculated for $C_{17}H_{20}N_2O_5$ Calculated: C 61.43%, H 6.07%, N 8.43%; Found: C 61.03%, H 6.15%, N 8.17%.

EXAMPLE 8

Dimethyl 3,3-(1′,5′(2′-ethyl-1′-pentenyl))-1,2,3,4,5,6-hexahydroazepino(4,5-b) indolinium-5,5-dicarboxylate bromide and tetraphenylborate (VIII; X=Br or tetraphenylborate)

To a solution of 200 mg (0.664 mmol) of amino diester (VIa) in 8 ml of dry methanol, stirring under $N_2$, was added 0,194 ml (1.32 mmol) of 5-bromo-2-ethyl-pentanal VIIa. The mixture was stirred for 8 hours at 40° C., then concentrated and the residue taken up in dichloromethane. Evaporation of the dichloromethane yielded a yellowish foam. Ethyl acetate was added and the foam was broken up into an off-white solid. The solid was filtered and washed with ethyl acetate under $N_2$, then dried under vacuum to yield 0.225 g (71%) of an off-white powder of the desired bromide (VIII).

IR (KBr, $v_{max}$): 3400, 2950, 1735 (broad), 1455, 1435, 1255 (broad), 750 cm⁻¹.

UV (EtOH, λ): 222, 284, 292 (sh) nm.

Since the solid is hygroscopic and decomposes in $CDCl_3$, the tetraphenylborate salt was prepared for analysis.

Solutions of 100 mg (0.209 mmol) of the spiro bromide (VIII) in 2 ml of dry methanol and of 72 mg (0.210 mmol) of sodium tetraphenylborate in 2 ml of dry methanol were prepared. These solutions were each filtered through glass wool plugs and the filters were rinsed with ∼1 ml of dry methanol. To the vigorously stirring spiro bromide solution was added at once the sodium tetraphenylborate solution. Upon addition the solution was clear yellow. After ~10 sec it became cloudy and a solid precipitated.

The suspension was stirred 0.5 hour then filtered and the solid washed with dry methanol and dried under vacuum to yield 120 mg (80%) of a white powder. The material resisted all attempts at crystallization, depositing an amorphous white solid from all solvent systems employed. From acetone/methanol the material has m.p. 244°–247° C.

Analysis calcultated for $C_{47}H_{49}N_2O_4B$ Calculated: C 78.76%, H 6.87%, N 3.91%; Found: C 78.93%, H 6.59%, N 3.69%.

IR (KBr, $\nu_{max}$): 3420 (broad), 3050, 3000, 2980, 1755 (sh), 1735, 1580, 1475, 1465, 1455 (sh), 1430, 1275, 1220, 775, 760, 740, 735, 710, 610 cm$^{-1}$.

EXAMPLE 9

Vincadifformine (Ia)

To a solution of 1 g (3.31 mmol) of the diesteramine VIa in 20 ml dry methanol, stirring under nitrogen, was added 0.533 ml (3.64 mmol, 0.703 g) of 5-bromo-2-ethylpentanal [see W. Oppolzer, H. Hauth, P. Pfaffli, R. Wenger Helv. 60, 1861 (1977)].

The solution was stirred 0.5 hour at room temperature then heated to 40° C., stirred for 5 hours, and then 1 ml of triethylamine was added. After 30 hours of continued stirring at 40° C. the solution was cooled and the solvent evaporated, leaving a viscous orange oil. Column chromatography on silica and eluting with ether yielded an oily product contaminated by unreacted bromoaldehyde. Crystallization from acetonitrile gave 0.285 g (26%) of vincadifformine (Ia), mp 124°–125° C.

IR (KBr, $\nu_{max}$): 3350, 2950, 2930, 2760, 1665, 1600, 1460, 1425, 1325, 1305, 1290, 1275, 1250, 1235, 1225, 1215, 1185, 1160, 1155, 1045, 755 cm$^{-1}$.

NMR (CDCl$_3$, $\delta$): 0.6 (t, 3H), 8.9–3.3 (m, 15H), 3.8 (s, 3H), 6.8–7.36 (m, 4H), 9.02 (bs, 1H).

Mass spectrum: (m/e) 338 (M+), 124 (100%).

Alternatively, the spiroenamonium bromide VIII, when stirred for 6 hours at 60° C. in methanol containing triethylamine gave vincadifformine, Ia, identified by matching of its spectroscopic data with those of the sample obtained above.

EXAMPLE 10

11-methoxyvincadifformine (Ib)

To a solution of 0.45 g (1.4 mmol) of diester amine VIb and 1 crystal of p-toluene sulfonic acid in 30 ml dry MeOH, stirring under N$_2$, was added 0.22 ml (0.29 g, 1.5 mmol) of bromoaldehyde VIIa. Stirring was continued for 0.5 hour at 20° C. and 10 hours at 40° C. At that time thin layer chromatography (SiO$_2$-5% methanol in dichloromethane) showed no starting material. To the solution 0.5 ml of triethylamine was added and the solution was heated to 60° C. and stirred for 4 hours. The solution was cooled to 20° C. and the solvent removed to yield an orange gummy solid. Chromatography (SiO$_2$ column with 5% methanol in dichloromethane) gave no separation. Therefore, the material was subjected to preparative thin layer chromatography on 2 mm SiO$_2$ plates, developping with ether. Collection of the bands at R$_f \approx$ 0.7, washing the silica with 10% methanol in ether, filtration and solvent removal yielded a white foam: 0.293 g (59%).

NMR (CDCl$_3$, $\delta$): 8.88 (bs, 1H), 7.04 (d, 1H), 6.36 (m, 2H), 3.74 (s, 6H), 3.27–0.69 (m, 14H), 0.55 (t, 3H).

IR (KBr): 3390, 1685, 1620, 1500, 1270 cm$^{-1}$.

MS (80 eV) m/e: 368 (M+), 124 (base)

UV (ethanol) $\lambda_{max}$ (log $\epsilon$): 249 (4.00), 330 (4.12).

Thin layer chromatography of this material (SiO$_2$-5% MeOH in CH$_2$Cl$_2$) showed one spot of R$_f \approx$ 0.4 which stained blue with ceric ammonium sulfate-phosphoric acid spray reagent.

The product crystallized from methanol with mp 90°–92° C. and formed a gummy hydrochloride when treated with ethereal HCl. Careful addition of methanolic HCl to a solution of the amine in methanol until the acid point was just reached, followed by removal of the methanol and trituration of the resultant oil with ether yielded an amorphous solid which also resisted crystallization. An IR spectrum of this solid showed the presence of a significant amount of saturated ester (1730 cm$^{-1}$) implying reaction of the $\beta$-anilino acrylate system with HCl.

Alternatively, a crystalline picrate was formed by addition of 53.8 mg of picric acid in the minimum amount of ethanol to 72 mg of the amine Ib also in the minimum amount of ethanol. Recrystallization from 95% ethanol gave an analytical sample with m.p. 183–184 (d)°C.

Analysis calculated for $C_{28}H_{31}N_5O_{10}$: Calculated: C 56.27%, H 5.23%, N 11.72%; Found: C 56.34%, H 5.47%, N 11.90%.

EXAMPLE 11

Synthesis of 2-ethyl-4-oxyranylpentanal VIIc (a) Methyl 2-ethyl-4-oxyranylpentanoate To methyl 2-ethyl-4,5-dehydropentanoate (3.85 g, 27 mmol) in methylene chloride (25 ml) at 0° C., was added m-chloroperbenzoic acid (6.5 g, 85%, 32 mmol). The solution was brought to room temperature and stirred for 12 h. The solid which had formed was filtered, washed with methylene chloride and the combined solutions were washed with saturated aqueous sodium carbonate, dried (MgSO$_4$) and concentrated. Distillation (100° C., 25 mm) of the crude oil gave the corresponding epoxide (3.5 g, 81%).

IR (neat): 2960, 1733, 1192, 1172 cm$^{-1}$.

NMR (CDCl$_3$) $\delta$ 0.90 (3H, t), 1.4–2.0 (4H, m), 2.38–2.68 (2H, m), 2.75 (1H, t), 2.95 (1H, m), 3.74 (3H, s).

(b) 2-ethyl-4-oxyranylpentanal VIIc

The epoxy-ester (2.08 g, 13.1 mmol) was placed in methylene chloride (20 ml) under nitrogen and cooled to −78° C. With vigorous stirring, diisobutyl aluminum hydride (1.2 equiv, 20% in hexane) was added dropwise over 10 min. The reaction was stirred for an additional 20 min, then quenched with methanol (2 ml) at −78° C. The solution was poured into water and extracted with methylene chloride. The aluminum salts which formed were separated by gravity filtration through glass wool and were washed with methylene chloride. The combined extracts were dried (MgSO$_4$) and concentrated in vacuo. Distillation (60°–65° C., 25 mm) gave 2-ethyl-4-oxyranylpentanal VIIc (925 mg, 55%).

IR (neat): 3055, 3023, 2910, 1720, 1450, 1260 cm$^{-1}$.

NMR (CDCl$_3$) $\delta$ 1.0 (3H, t), 1.1–2.1 (4H, m), 2.3–2.6 (2H, m), 2.85 (1H, t), 3.05 (1H, m), 9.85 (1H, d).

EXAMPLE 12

14-hydroxyvincadifformine Ic and 14-hydroxymethyl-E-norvincadifformine Id

Azepino-indole VIa (460 mg, 2.1 mmol) and 0.5 ml of triethylamine and epoxyaldehyde VIIc (0.5 g, 3.9 mmol) were refluxed under nitrogen in methanol (10 ml) for 8 h. The methanol was removed in vacuo. Compound Id crystallized out after resting overnight. It was recrystallized from acetonitrile; m.p. 153°–154° C. (503 mg, 68%). The remaining residue was purified by preparative thin layer chromatography (silica gel, 3% methanol in methylene chloride, rf 0.6 for Ic and 0.15 for Id) yielding a second component (Ic) as an amorphous solid (105 mg, 14%).

For Id: IR (KBr) 3260, 2950, 1682, 1605 cm$^{-1}$; UV (MeOH) nm 226, 298, 328; MS (m/e) 354 (M+).

For Ic: IR (film) 3360 (broad), 2950, 2790, 1640, 1600 cm$^{-1}$; UV (MeOH) nm 228, 298, 328; MS (m/e) 354 (M+).

EXAMPLE 13

Synthesis of 4-(bromomethyl)hexanal VIIb (a) 4-ethyl-5-hydroxypentanoic acid lactone Methyl 4-formyl hexanoate (15.3 g, 97 mmol) was cooled to 0° C. in anhydrous methanol (125 ml) and sodium borohydride (1.84 g, 48 mmol) was added at a rate such that the reaction stayed below 20° C. The solution was stirred for 30 min after the addition was completed and then was poured into water. The aqueous solution was extracted with ether (3×75 ml). The combined extracts were washed with saturated brine, dried (MgSO$_4$) and concentrated in vacuo. The oil was taken up in benzene (200 ml) and p-toluenesulfonic acid (1 g) was added. The solution was refluxed for 15 h. using a Dean-Stark trap filled with anhydrous calcium chloride. After cooling the reaction mixture was washed with saturated sodium bicarbonate, dried (MgSO$_4$) and the solvent evaporated. Distillation of the crude material gave 4-ethyl-5-hydroxypentanoic acid lactone bp 70°–75° C. (0.25 mm) (7.2 g, 58%).

IR (neat): 2968, 1730, 1180, 1056 cm$^{-1}$.

NMR (CDCl$_3$) δ 0.98 (3H, t), 1.2–2.2 (5H, m), 2.58 (2H, m), 4.0 (1H, d of d), 4.35 (1H, m).

(b) Methyl 4-(bromomethyl)hexanoate

Anhydrous HBr gas was bubbled into the 4-ethyl-5-hydroxypentanoic acid lactone (3 g, 23 mmol) at 60° C. for 30 min. The solution was allowed to cool and methanol (15 ml) with trimethylorthoformate (2.5 g, 23 mmol) was added. The solution was stirred for 8 h., then concentrated and distilled, bp 70°–75° C. (0.1 mm) to produce the desired bromoester (4.3 g, 83%).

IR (neat): 2955, 1733, 1170 cm$^{-1}$.

NMR (CDCl$_3$) δ 0.98 (3H, t), 1.3–2.0 (5H, m), 2.45 (2H, t), 3.6 (2H, d), 3.82 (3H, s).

(c) 4-(bromomethyl)hexanal VIIb

The above mentioned bromoester (1.9 g, 8.5 mmol) was dissolved in anhydrous methylene chloride (20 ml) and cooled with vigorous stirring to −78° C. Diisobutylaluminum hydride (10.2 ml, 1 M in hexane) was added dropwise over 10 min. The solution was stirred for an additional 20 min at −78° C. and then quenched by the addition of methanol (2 ml). The solution was poured into 3% HCl, extracted with methylene chloride (3×30 ml) and dried (MgSO$_4$). Solvent removal gave a light oil which was purified by distillation, bp 78° C. (0.4 mm) (1.38 g, 84%).

IR (neat): 2959, 2720, 1720 cm$^{-1}$.

NMR (CDCl$_3$) δ 0.97 (3H, t), 1.3–2.0 (5H, m), 2.57 (2H, t), 3.6 (2H, d), 10.15 (1H, t).

EXAMPLE 14

Pseudo vincadifformine Ie (14-ethyl-18,19-dinorvincadifformine) and epi-14-pseudovincadifformine Ie'

Azepino-indole VIa (0.92 g, 4.1 mmol) was dissolved in methanol (30 ml) at room temperature and bromoaldehyde VIIb (1.0 g, 5.3 mmol) was added. The solution was stirred for 4 hours at which time, triethylamine (1 ml, excess) was added and the solution was heated at 40° C. with stirring for 16 h.

The methanol was removed "in vacuo" and the residue was taken up in methylene chloride (75 ml), washed with saturated aqueous sodium carbonate, dried (MgSO$_4$) and concentrated. HPLC (using a 10 inch commercial microporacil column with a flow rate of 0.9 ml/min eluting with chloroform, showed two components Ie (retention time: 10.3 min) and Ie' (retention time: 8.5 min) with a ratio of 4:1 which correspond to the two components (ratio 4:1) in a sample of natural pseudo-vincadifformine. Medium pressure column chromatography (4ft×1.25 in., silica gel eluting with chloroform allowed isolation of the major isomer as a homogeneous material (by HPLC) which was induced to crystallize by trituration in methanol-water. This was recrystallized from methanol-water (95:5), m.p. 118°–119° C. (155 mg, 11%). Enrichment of the remaining mixture of epimers (415 mg, 30%) by selective crystallization produces mixture of no better than a 1:1 ratio.

For Ie: IR (KBr): 3365, 2955, 2773, 1666, 1605, 740 cm$^{-1}$.

NMR (CDCl$_3$) δ 0.95 (3H, t), 1.1–1.6 (4H, m), 1.6–2.15 (4H, m), 2.15–2.65 (3H, m), 2.65–2.95 (4H, m), 3.68 (3H, s), 6.5–6.7 (2H, m), 6.8–7.2 (2H, m), 8.7 (1H, broad).

UV (methanol) nm: 228, 298, 328. For a mixture of Ie and Ie' (ca 1:1) the NMR spectrum shows a shift of absorbances indicating more protons in the region of δ 1.6–2.5 and fewer in the region of δ 1.1–1.6.

What I claim is:

1. A process for the preparation of vincadifformine or related compound of the formula I

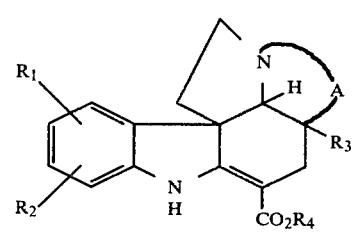

wherein each $R_1$ and $R_2$ individually is hydrogen, or hydroxy, or carbamate, or lower alkoxy, or lower alkyl having from one to 7 carbon atoms, or halo, or a combination of such substituents; $R_3$ and $R_4$ are the same or different and are hydrogen or alkyl having from one to 7 carbon atoms; A represents an alkyl chain or from 2 to 5 carbon atoms and which may be substituted by at least one alkyl, hydroxy, or hydroxy-alkyl groups of from 1 to 7 carbon atoms, characterised in condensing a dialkyl 1,2,3,4,5,6-hexahydroazepino (4,5-b) indole-5,5-dicarboxylate of the formula VI

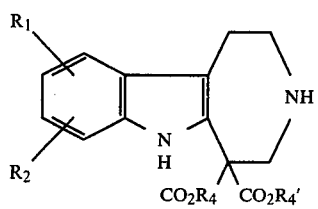

wherein $R_1$, $R_2$ and $R_4$ are as defined above, and $R'_4$ is as defined for $R_4$; with a straight chain or branched chain aldehyde selected from the group of halo aldehyde, arylsulfoxy aldehyde, lower alkylsulfoxy aldehyde or epoxy aldehyde and having from three to fourteen carbon atoms to produce vincadifformine or a related compound of the formula I.

2. A process for the preparation of vincadifformine or related compound of the formula I

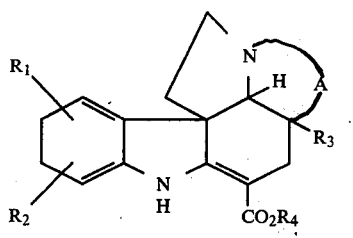

wherein each $R_1$ and $R_2$ individually is hydrogen, or hydroxy, or carbamate, or lower alkoxy, or lower alkyl having from one to 7 carbon atoms, or halo, or a combination of such substituents; $R_3$ and $R_4$ are the same or different and are hydrogen or alkyl having from one to 7 carbon atoms; A represents an alkyl chain from 2 to 5 carbon atoms and which may be substituted by at least one alkyl, hydroxy, or hydroxy-alkyl groups of from 1 to 7 carbon atoms, characterised in condensing a dialkyl 1,2,3,4,5,6-hexahydroazepino(4,5-b)indole-5,5-dicarboxylate of the formula VI

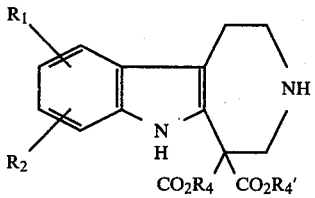

wherein $R_1$, $R_2$, and $R_4$ are as defined above, and $R'_4$ is as defined for $R_4$; with a straight chain or branched chain aldehyde selected from the group of halo aldehyde, arylsulfoxy aldehyde, lower alkoxysulfoxy aldehyde or epoxy aldehyde and having from three to fourteen carbon atoms to produce vincadifformine or a related compound of the formula I;

and which further includes reacting a N-benzyltetrahydro-γ-carboline of the formula III

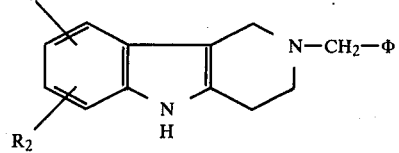

wherein $R_1$ and $R_2$ are as defined above and $\phi$ means phenyl with t-butyl hypochlorite to obtain a halogenoindolenine; directly treating said halogenoindolenine with a sodium dialkyl malonate or thallium dialkyl malonate to thereby provide a dialkyl 3-benzyl-1,2,3,4,5,6-hexahydroazepino(4,5-b)indole-5,5-dicarboxylate of the formula V:

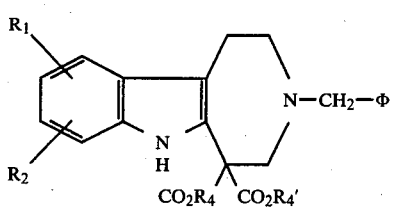

hydrogenating the compound of formula V in the presence of a palladium on charcoal hydrogenation catalyst to provide the dialkyl 1,2,3,4,5,6-hexahydroazepino(4,5-b)indole-5,5-dicarboxylate (VI).

3. A process for preparing dialkyl 1,2,3,4,5,6-hexahydroazepino(4,5-b)indole-5,5-dicarboxylate characterized by reacting a N-benzyl-tetrahydro-γ-carboline (III) with t-butyl hypochlorite to obtain a halogenoindolenine directly treating said halogenoindolenine with a sodium or a thallium dialkyl malonate to provide a dialkyl 3-benzyl-1,2,3,4,5,6-hexahydroazepino(4,5-b)indole-5,5-dicarboxylate (V);

hydrogenating the compound (V) in the presence of a palladium on charcoal hydrogenation catalyst to provide a dialkyl 1,2,3,4,5,6-hexahydroazepino(4,5-b)indole-5,5-dicarboxylate (VI).

4. A process according to claim 1, characterized in that the dialkyl 1,2,3,4,5,6-hexahydroazepino(4,5-b)indole-5,5-dicarboxylate compound of formula VI is obtained by hydrogenolytic cleavage of the N-benzyl substituent of a dialkyl 3-benzyl-1,2,3,4,5,6-hexahydroazepino(4,5-b)indole-5,5-dicarboxylate of the formula

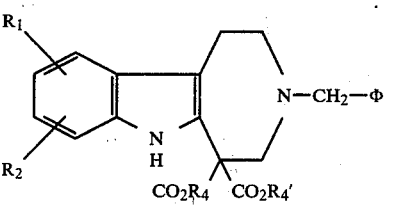

in which $R_1$, $R_2$, $R_4$ and $R_4'$ have the above indicated meanings and Φ means phenyl.

5. A process according to claim 4, characterised in that the dialkyl 3-benzyl-1,2,3,4,5,6-hexahydroazepino(4,5-b)indole-5,5-dicarboxylate compound of formula V is obtained from a N-benzyl-tetrahydro-γ-carboline of the formula

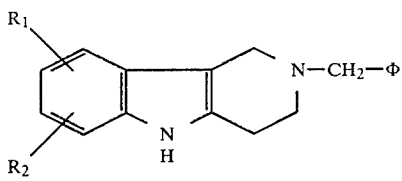

on which $R_1$, $R_2$ and $\Phi$ have the above indicated meanings through a chloroindolenine of the formula

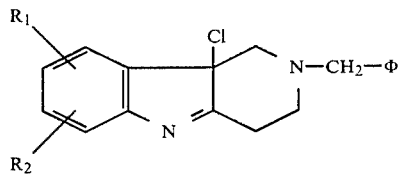

6. A process for preparing vincadifformine or a vincadifformine derivative (I) characterised by the steps of:
transforming a N-benzyl-piperidone into a N-benzyl-tetrahydro-γ-carboline (III);
transforming compound (III) into a dialkyl 1,2,3,4,5,6-hexahydroazepino(4,5-b)indole-5,5-dicarboxylate (VI);
transforming compound (VI) into a vincadifformine (I).

7. The process of claim 2 wherein said halogenoindolenine is a chloroindolenine of the formula IV

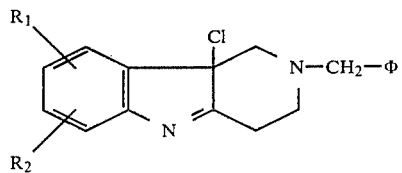

8. The process of claim 2 wherein said aldehyde is a halo aldehyde or epoxy aldehyde.

9. The process of claim 2 wherein said aldehyde includes 5-bromo-2-ethyl pentanal, or 5-chloro-2-ethyl-pentanol, or 5-sulfo-methoxy-2-ethyl pentanal, or 4-(bromomethyl)hexanol or 2-ethyl-4-oxyranyl pentanal.

10. The process of claim 2 wherein the temperature of said condensing is from −20° C. to the boiling point of the reaction medium.

11. The process of claim 2 wherein the temperature of said condensing is 20° C. to 40° C.

12. The process of claim 1 wherein the temperature of said condensing is from −20° C. to the boiling point of the reaction medium.

13. The process of claim 1 wherein the temperature of said condensing is 20° C. to 40° C.

14. The process of claim 2 which is further characterized by transforming a N-benzyl-piperidene into said N-benzyl-tetrahydro-γ-carboline (III).

15. The process of claim 1 wherein said aldehyde is a halo aldehyde or epoxy aldehyde.

16. The process of claim 1 wherein said aldehyde includes 5-bromo-2-ethyl pentanal, or 5-chloro-2-ethylpentanol, or 5-sulfo-methoxy-2-ethyl pentanal, or 4-(bromomethyl)hexanol or 2-ethyl-4-oxyranyl pentanal.

17. The process of claim 2 wherein said metal dialkyl malonate is a thallium dialkyl malonate.

18. The process of claim 17 wherein said malonate is a diethyl or dimethyl malonate.

19. The process of claim 2 wherein said malonate is a diethyl or dimethyl malonate.

20. The process of claim 3 wherein said metal dialkyl malonate is a thallium dialkyl malonate.

21. The process of claim 20 wherein said malonate is a diethyl or dimethyl malonate.

22. The process of claim 3 wherein said malonate is a diethyl or dimethyl malonate.

23. The process of claim 2 wherein $R_1=R_2=H$, $R_3=CH_2-CH_3$, $A=-(CH_2)_3-$, $R_4=CH_3$ 24. The process of claim 2 wherein $R_1=11-OCH_3$, $R_2=H$, $R_3=CH_2-CH_3$, $R_4=CH_3$, $A=-(CH_2)_3-$ 25. The process of claim 2 wherein $R_1=R_2=H$, $R_3=CH_2-CH_3$, $R_4=CH_3$, $A=-CH_2-CH(OH)-CH_2-$ 26. The process of claim 2 wherein $R_1=R_2=H$, $R_3=CH_2-CH_3$, $R_4=CH_3$, $>N-A-=-N-CH(CH_2OH)-CH_2-$ 27. The process of claim 2 wherein $R_1=R_2=H$, $R_3=H$, $R_4=CH_3$, $A=-CH_2-CH(CH_2-CH_3)-CH_2-$ 28. The process of claim 2 wherein said aldehyde is a halo or epoxy aldehyde; and the temperature of said condensing is from −20° C. to the boiling point of the reaction medium.

29. The process of claim 1 or 2 wherein A represents an alkyl chain of 2 or 3 carbon atoms.

* * * * *